United States Patent [19]

Batcho

[11] Patent Number: 4,506,078
[45] Date of Patent: Mar. 19, 1985

[54] 7-NITROINDOLES

[75] Inventor: Andrew D. Batcho, North Caldwell, N.J.

[73] Assignee: Hoffmann-La Roche Inc., Nutley, N.J.

[21] Appl. No.: 270,718

[22] Filed: Jun. 5, 1981

[51] Int. Cl.³ .......................................... C07D 209/08
[52] U.S. Cl. .................................................. 548/469
[58] Field of Search ...................... 260/319.1, 326.16; 548/469, 508

[56] References Cited

U.S. PATENT DOCUMENTS 3,226,396 12/1965 Johnson .............................. 548/492
3,732,245 5/1973 Batcho et al. ....................... 548/508
3,976,639 8/1976 Batcho et al. ....................... 549/439

Primary Examiner—Glennon H. Hollrah
Assistant Examiner—D. B. Springer
Attorney, Agent, or Firm—Jon S. Saxe; Bernard S. Leon; Matthew Boxer

[57] ABSTRACT

7-Aminoindole is prepared from a 7-nitroindole, which in turn is prepared from a halo-substituted β-dialkylamino-2-nitrostyrene.

2 Claims, No Drawings

7-NITROINDOLES

SUMMARY OF THE INVENTION

This invention relates to processes and intermediates for the preparation of 7-aminoindole which is a compound of the formula

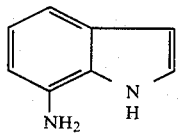

I

In another aspect, the invention relates to processes and intermediates for the preparation of 7-nitroindoles of the formula

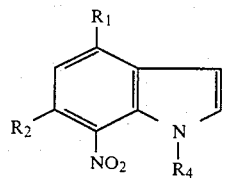

VII wherein at least one of $R_1$ and $R_2$ is halogen and the other is hydrogen or halogen and $R_4$ is hydrogen, lower alkoxy, or hydroxy.

The compounds of formula VII can be converted to compounds of formula I as described herein.

More particularly, the invention involves cyclizing a β-dialkylamino-2,3-dinitrostyrene compound, which may be halogenated at the 4- or 6-position, or the hydrolyzate thereof, by reacting it with ammonium hydroxide or an amine of the formula $R_4NH_2$, wherein $R_4$ is as previously described. The 7-nitroindole is treated with a reducing agent to produce 7-aminoindole.

The β-dialkylamino-2,3-dinitrostyrene and its hydrolyzate, which is the corresponding 2,3-dinitrophenylacetaldehyde, can be prepared by several methods described herein.

DETAILED DESCRIPTION OF THE INVENTION

As used herein, the term "lower alkyl" denotes a straight or branched chain saturated hydrocarbon containing one to seven carbon atoms, for example, methyl, ethyl, propyl, isopropyl, butyl, t-butyl, neopentyl, pentyl, heptyl, and the like. The term "lower alkoxy" denotes an alkyl ether group in which the lower alkyl group is as described above, for example, methoxy, ethoxy, propoxy, pentoxy, and the like. The term "halogen" or "halo" denotes the four halogens, i.e. bromine, chlorine, fluorine and iodine.

A preferred embodiment of the invention is illustrated with reference to Raction Sequence I:

Reaction Sequence I

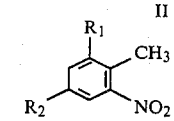

II (a)

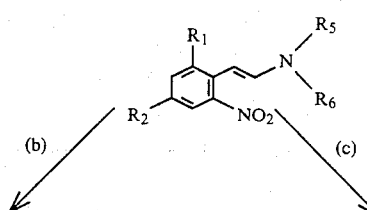

III (b)        (c)

 IV (d)

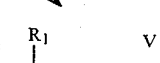 V (e)

(f)        (g)

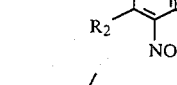 VI (h)

 VII (i)        (j)

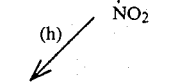 Ia

 (k)  I wherein $R_1$, $R_2$ and $R_4$ are as previously defined; $R_3$ is lower alkyl and $R_5$ and $R_6$ are each individually lower alkyl.

In Reaction Sequence I, the nitrotoluene of formula II, which is a known compound and can be prepared according to known procedures, is treated with N,N-dialkylformamide dialkylacetal in the presence of a solvent to yield the corresponding trans-β-dialkylamino-2-nitrostyrene of formula III. This is a known reaction which is described in greater detail in U.S. Pat. No. 3,732,245.

The compound of formula III is treated with a nitrating agent to produce compounds of formulas IV and V. Suitable nitrating agents are well known to those skilled in the art and include, by way of example, nitric acid in sulfuric acid, acetic acid, or acetic anhydride; and alkali metal nitrates, e.g. sodium nitrate, potassium nitrate and the like, in sulfuric acid. Temperature of the nitration reaction is not narrowly critical and the nitration reaction can conveniently be carried out at room temperature or above, preferably at 50°–70° C.

The aldehyde of formula V is produced by the hydrolysis of the compound of formula IV or by the hydrolysis of the compound of formula III and subsequent nitration of the hydrolyzate. The by-product water produced during nitration, i.e. in steps (b) and (c), normally results in the occurence of such hydrolysis reactions in the reaction mixture so that the reaction mixture contains both compounds IV and V. In order to simplify recovery of the product, we prefer to convert the compound of formula IV in the reaction mixture to the aldehyde of formula V by hydrolysis prior to recovering the product. This can be easily achieved, for example, by pouring the nitration reaction mixture over a mixture of water and ice. Hydrolysis then occurs upon standing. The compound of formula V can be recovered by conventional methods known in the art, for example, by crystallization from a suitable solvent such as benzene-hexane, diethyl ether-petroleum ether, methylene chloride-hexane, etc.

If the compound of formula V is crystallized from a lower-alkyl alcohol, e.g. methanol, ethanol, isopropanol, or the like, the product is recovered as the corresponding alkoxyethanol, i.e. the compound of formula VI, which can also be converted to the 7-nitroindole of formula VII.

Compounds of formulas IV, V, or VI, or any mixture of such compounds, are cyclized by reacting with ammonium hydroxide or an amine of the formula $R_4NH_2$, wherein $R_4$ is as previously defined, to yield the 7-nitroindole of formula VII. The reaction can be carried out in the presence of any conventional solvent which does not interfere with the reaction. Useful solvents include, for example, ethers such as tetrahydrofuran, diethyl ether, etc. or alcohols such as methanol, ethanol, etc. Temperature of the reaction is not narrowly critical and the reaction can be conducted at a temperature ranging from about room temperature to 200° C. or higher, and is preferably conducted at about the reflux temperature of the solvent. The reaction may be effected at atmospheric or super-atmospheric pressures. The product of the cyclization reaction, i.e. the 7-nitroindole of formula VII, can be recovered by conventional means such as crystallization from an organic solvent.

Compounds of formulas V, VI, and VII are novel compounds within the scope of this invention.

The 7-nitroindole, i.e. the compound of formula VII, is reduced, for example by catalytic hydrogenation, to produce the compounds of formula I or Ia. Hydrogenation may be effected in a conventional manner. Temperature of the reaction is not critical, conveniently hydrogenation can be effected at room temperature with a hydrogen pressure of from 1 to about 10 atmospheres. Any suitable hydrogenation catalyst may be employed, for example, a metal selected from the group consisting of chromium, molybdenum, tungsten, platinum, palladium, rhodium, cobalt, nickel, and ruthenium, their oxides, and combinations thereof. Conveniently, the catalyst may be supported on charcoal, carbon, or the like.

Advantageously, the catalyst may be utilized in the presence of an inert solvent, for example, an alkanol such as methanol, ethanol, or the like; a hydrocarbon such as benzene, toluene, or the like; ethyl acetate; or dimethylformamide.

The particular hydrogenation conditions employed determine whether the substituents $R_1$ and $R_2$ undergo a chemical change during the hydrogenation. If one desires to obtain the compound of formula I, i.e. 7-aminoindole having no halo substituent in the benzene moiety, the hydrogenation of the compound of formula VII is preferably conducted in the presence of a base such as sodium hydroxide or a tertiary amine, e.g. trimethylamine, triethylamine or the like. A preferred hydrogenation catalyst for the preparation of the compound of formula I is palladium on charcoal. Preferably, the hydrogenation is effected at a temperature of from about 0° C. to 50° C.

If one desires to produce a compound of formula Ia, i.e. a 7-aminoindole which retains halo substitution in the benzene moiety, the hydrogenation of the compound of formula VII is preferably carried out in the absence of base. Preferred hydrogenation catalysts for the preparation of the compounds of formula Ia are Raney nickel and platinum. The hydrogenation to produce the compounds of formula Ia is preferably effected at a temperature of from about 0° C. to 50° C.

The 7-aminoindoles of formula Ia can be converted to 7-aminoindoles by hydrogenation in the presence of a base in a manner analogous to that described above for the conversion of the compounds of formula VII.

The 7-aminoindoles of formula Ia can also be prepared by the chemical reduction of the compounds of formula VII, for example, with a metal such as iron, zinc, tin, and the like, in an organic or inorganic acid such as acetic acid, hydrochloric acid, and the like; stannous chloride in hydrochloric acid; ferrous sulfate; sodium dithionite; sodium or ammonium sulfide or hydrosulfide; and the like. The reaction conditions of the chemical reduction are not narrowly critical. Preferably, it is effected at a temperature in the range of between about room temperature and the reflux temperature of the reaction mixture, in the presence of a solvent such as water, or water miscible solvents, for example, alkanols such as methanol, ethanol or the like, or tetrahydrofuran.

Upon completion of the reduction of the 7-nitroindoles of formula VII by hydrogenation or by chemical reduction, the 7-aminoindoles of formulas I or Ia can be recovered by conventional means such as crystallization, distillation, and the like.

A second embodiment of this invention is illustrated with reference to reaction sequence II:

Reaction Sequence II

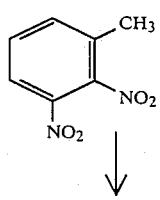

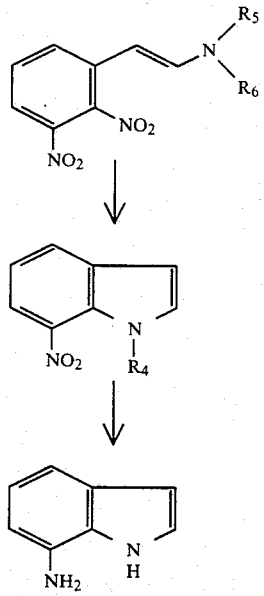

wherein R₄, R₅ and R₆ are as previously described.

The starting material in Reaction Sequence II, i.e. 2,3-dinitrotoluene, is a known material which can be prepared according to procedures dislosed in Memorial Des Poudres, 45, p. 7(1965).

The conversion of 2,3-dinitrotoluene to a compound of formula IVa is effected by reacting 2,3-dinitrotoluene with N,N-dialkylformamide dialkyl acetal in a manner analogous to the conversion of the compound of formula II to the compound of formula III as shown in Reaction Sequence I.

The conversion of a compound of formula IVa to a compound of formula VIIa is effected by reacting a compound of formula IVa with ammonium hydroxide or an amine of the formula R₄NH₂ wherein R₄ is as previously described, in a manner analogous to the conversion of a compound of formula IV to a compound of formula VII as shown in Reaction Sequence I.

The conversion of a compound of formula VIIa to a compound of formula I is effected by reduction in a manner analogous to that employed to convert a compound of formula VII to a compound of formula I as shown in Reaction Sequence I.

The 7-aminoindoles of formulas I and Ia which are prepared by the processes described hereinabove, are known compounds which have commercial utility. For example, they are useful as photographic dyes, as described in more detail in U.S. Pat. No. 3,702,244.

The Examples which follow further illustrate the invention. All temperatures are in degrees Centigrade, unless otherwise specified.

EXAMPLE 1

Preparation of trans-6-chloro-β-dimethylamino-2-nitrostyrene

A 2-liter flask fitted with a 30-cm. vacuum-jacketed Vigreux column, downward condenser, and receiver with a nitrogen inlet was charged with 171.6 g. of 6-chloro-2-nitrotoluene, 500 ml. of dimethylformamide, and 149.0 g. of N,N-dimethylformamide dimethyl acetal and then heated to 140°–156° for 13 hours. The pot temperature was maintained by continuous distillation of the methanol as it was formed.

The solvent and volatile components were removed in vacuo and the residue, 232.0 g. of trans-6-chloro-β-dimethylamino-2-nitrostyrene, was used directly in the next step, set forth in Example 2.

EXAMPLE 2

Preparation of 6-chloro-β-dimethylamino-2,3-dinitrostyrene

To a stirred solution of 13.9 ml. of conc. sulfuric acid and 2.41 ml. of 70% nitric acid at 25° was added 2.2 g. of 6-chloro-β-dimethylamino-2-nitrostyrene dropwise over a period of 6 minutes. The red-brown solution was then placed in a water bath at 55° for 30 minutes. The pale brown solution was poured into a vigorously stirred solution of 80 ml. of 7N sodium hydroxide and 250 g. crushed ice; the resulting suspension was extracted with three 100 ml. portions of methylene chloride and each was washed with 100 ml. of water in a countercurrent manner. The combined methylene chloride phases were dried over sodium sulfate, filtered, and evaporated to give a dark red oil. On crystallization from boiling methanol, an unsoluble, colorless solid which formed was removed by filtration; from the filtrate, on cooling, were deposited red crystals which were recrystallized from 10 ml. of methanol to give 143 mg. of 6-chloro-β-dimethylamino-2,3-dinitrostyrene, having a melting point of 109.5°–111°.

EXAMPLE 3

Preparation of 6-chloro-2,3-dinitrophenylacetaldehyde

To a stirred solution of 109 ml. of conc. sulfuric acid and 24.0 ml. of 70% nitric acid was added 23.2 g. of crude 6-chloro-β-dimethylamino-2-nitrostyrene dropwise over a period of 15 minutes while maintaining the temperature below 15°. The dark solution was heated at 60° for 1 hour, and then poured into a mixture of 1.5 kg. of ice and 1 l. of water. The suspension was extracted immediately with three 250 ml. portions of chloroform and then again after 2 and 4 hours respectively. Each chloroform extract was washed in a countercurrent manner with two 500 ml. portions of water. The chloroform extracts yielded, on evaporation of the solvent, three fractions, respectively, 3.3 g., 17.75 g. and 1.5 g.

The second fraction of 17.75 g., on trituration with ether (2×20 ml.), gave 8.5 g. of crystals. Recrystallization from ether gave 2.9 g. of white crystals; the mother liquors, after evaporation of the solvent, sublimation at 100°/0.5 mmHg, and crystallization from methylene chloride-ether, afforded an additional 1.33 g. of 6-chloro-2,3-dinitrophenylacetaldehyde, as white crystals having a melting point of 79°–80°. The 6-chloro-2,3-dinitrophenylacetaldehyde can be converted to a 7-nitroindole by reacting it with ammonia, ammonium hydroxide or an amine of the formula R'₄NH₂.

EXAMPLE 4

Preparation of 2-(6-chloro-2,3-dinitrophenyl)-1-methoxyethanol

To a stirred solution of 34 g. of 70% nitric acid in 256 g. of sulfuric acid at 55° was added dropwise 23.2 g. of crude trans-6-chloro-β-dimethylamino-2-nitrostyrene as rapidly as possible, about 15 minutes, while maintaining the temperature at 55°–60°. The resulting solution was heated at 55° for 1 hour and then was poured onto about 4 l. of ice and water. Some precipitation occurred. The suspension was extracted with 500 ml. of chloroform. The phases were separated and the chloroform phase was successively washed with 100 ml. of 1N sodium bicarbonate and 250 ml. of water. The extraction was repeated maintaining the temperature below 10°, adding 500 ml. of chloroform immediately after each phase separation, and shaking several times during the interval as follows:

| Time after quenching | Wt. extracted |
| --- | --- |
| 5 min. | 6.7 g. |
| 35 min. | 5.6 g. |
| 85 min. | 5.3 g. |
| 125 min. | 1.9 g. |
| 205 min. | 0.6 g. |

Thus, a total of 20.1 g. of dark amber solid was obtained. This material was dissolved in 10 ml. of methanol, and within a few minutes crystallized to a thick paste which was recrystallized from 80 ml. of chloroform. The mother liquor was evaporated in a rotary evaporator and the residue was recrystallized from methanol-chloroform as above. In this way, 15.5 g. (56%) of amberish crystals was obtained in 3 crops. Recrystallization from 100 ml. of chloroform, after treatment with charcoal (Darco KB) and filtration through Celite followed by the addition of 10 ml. of methanol prior to cooling, gave 13.84 g. (50%) of 2-(6-chloro-2,3-dinitrophenyl)-1-methoxyethanol as almost white crystals having a melting point of 131°-132°.

EXAMPLE 5

Preparation of 4-chloro-7-nitroindole

To a slurry of 13.83 g. of 2-(6-chloro-2,3-dinitrophenyl)-1-methoxyethanol in 100 ml. of methanol under nitrogen was added 10.0 ml. of ammonium hydroxide (28.6% ammonia). The resulting brown suspension was heated at reflux for 1½ hours and then an additional 10.0 ml. of conc. ammonium hydroxide was added and the reflux period continued for one more hour. Most of the methanol was removed on a rotary evaporator under reduced pressure and the resulting slurry was diluted with water (about 30 ml.) and filtered to give, after drying, 11.35 g. of brown crystals. The filtrate was diluted with water to about 100 ml. and was extracted with two 50 ml. portions of chloroform. The chloroform phases were washed with 50 ml of water and evaporated to give 0.60 g. of brown solid. The combined solids were crystallized from 150 ml. of methanol [decolorized with 1.0 g. of charcoal (Darco KB) for 10 minutes] to give, in three crops, 7.15 g. (73%) of 4-chloro-7-nitroindole as yellow crystals having a melting point of 165.5°-167°.

EXAMPLE 6

Preparation of 7-aminoindole

To a slurry of 1.96 g. of 4-chloro-7-nitroindole in 100 ml. of methanol containing 400 mg. of sodium hydroxide in a 500-ml. Parr bottle was added 196 mg. of 10% palladium on charcoal. The suspension was shaken for 2½ hours under an initial hydrogen pressure of 3 atmospheres (absorption ceased after 1½ hours). The catalyst was removed by filtration and the pale yellow solution was evaporated on a rotary evaporator under reduced pressure. The residue was partitioned between 75 ml. of toluene and 35 ml. of water, and the toluene layer washed with 35 ml. of water. The water phases were then extracted with three 75 ml. portions of chloroform. The toluene and chloroform extracts were evaporated to give 950 mg. and 420 mg. respectively, of greyish crystals. On sublimation on the steambath at 0.08 mm., 567 mg. (43%) of 7-aminoindole having a melting point of 98°-99° was obtained.

EXAMPLE 7

Preparation of 4-chloro-7-nitroindole

To a solution of 272 mg. (1.0 mmol) of 6-chloro-β-dimethylamino-2,3-dinitrostyrene in 10 ml. of methanol at reflux was added 1 ml. of ammonium hydroxide (28% ammonia). After 1 hour, an additional 1 ml. of ammonium hydroxide was added. After six hours, the reaction mixture was poured into 100 ml. of water and extracted with methylene chloride (2×50 ml.). The combined methylene chloride extracts were dried over sodium sulfate, filtered, and evaporated on a rotary evaporator. The residue (150 mg.) was chromatographed on 15 g. of silica gel. Elution with 1:1 hexane-ether gave 30 mg. of 4-chloro-7-nitroindole, as yellow crystals, mp 166°-167°.

EXAMPLE 8

Preparation of β-dimethylamino-2,3-dinitrostyrene

A 250-ml. flask fitted with 22-cm. vacuum-jacketed, silvered Goodloe column, distillation head, and receiver with nitrogen inlet was charged with 36.4 g. of 2,3-dinitrotoluene, 49.6 g. of N,N-dimethylformamide dimethyl acetal, and 100 ml. of N,N-dimethylformamide and then was heated to 140°-156° for 2½ hours. The solvent and volatile components were removed in vacuo and the residue (45.65 g.) was recrystallized from 40 ml. of acetonitrile and gave, in two crops, 22.55 g. (47%) of β-dimethylamino-2,3-dinitrostyrene as dark violet crystals having a melting point of 128°-130°.

EXAMPLE 9

Preparation of 7-nitroindole

A 20-ml autoclave was charged with 237 mg. (1.0 mmol) of β-dimethylamino-2,3-dinitrostyrene, 2 ml. of 28% ammonium hydroxide, and 10 ml. of methanol, pressurized to 345 psi, and heated at 150° for 15 hours. The solvents were removed under reduced pressure and the residue, 185 mg., was chromatographed on 12 g. of silica gel. Elution with 1:1 ether-hexane afforded 86 mg. of 7-nitroindole as yellow crystals, mp 92°-93°.

I claim:

1. A compound of the formula

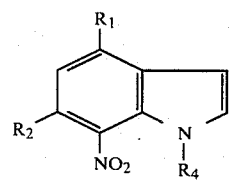

VII wherein at least one of $R_1$ and $R_2$ is halogen and the other is halogen or hydrogen, and $R_4$ is hydrogen.

2. The compound in accordance with claim 1, 4-chloro-7-nitroindole.

* * * * *